(12) United States Patent
Rump et al.

(10) Patent No.: US 11,083,890 B2
(45) Date of Patent: Aug. 10, 2021

(54) PASSIVE FIXATION OF AN IMPLANTABLE ELECTRODE LEAD BY MEANS OF COMPRESSIBLE ANCHORING ELEMENTS

(71) Applicant: BIOTRONIK SE & Co. KG, Berlin (DE)

(72) Inventors: Jens Rump, Berlin (DE); Torsten Luther, Teltow (DE)

(73) Assignee: BIOTRONIK SE & Co. KG, Berlin (DE)

( * ) Notice: Subject to any disclaimer, the term of this patent is extended or adjusted under 35 U.S.C. 154(b) by 45 days.

(21) Appl. No.: 16/402,830

(22) Filed: May 3, 2019

(65) Prior Publication Data

US 2019/0351217 A1    Nov. 21, 2019

(30) Foreign Application Priority Data

May 16, 2018   (DE) ...................... 10 2018 111 741.8

(51) Int. Cl.
*A61N 1/05* (2006.01)
(52) U.S. Cl.
CPC .................................. *A61N 1/059* (2013.01)
(58) Field of Classification Search
CPC ...... A61N 1/0573; A61N 1/0558; A61N 1/05; A61N 1/059; A61N 1/057
See application file for complete search history.

(56) References Cited

U.S. PATENT DOCUMENTS

| 6,240,322 | B1 * | 5/2001 | Peterfeso | A61N 1/057 |
| | | | | 607/126 |
| 2004/0068299 | A1 | 4/2004 | Laske et al. | |
| 2006/0095078 | A1 * | 5/2006 | Tronnes | A61N 1/37205 |
| | | | | 607/2 |
| 2010/0125320 | A1 | 5/2010 | Polkinghorne et al. | |
| 2010/0324637 | A1 | 12/2010 | Trip et al. | |

FOREIGN PATENT DOCUMENTS

| DE | 102005039040 A1 | 2/2007 |
| DE | 102013224283 A1 | 6/2015 |

OTHER PUBLICATIONS

German Search Report for German Case No. DE 10 2018 111 741.8, dated Jun. 27, 2018 (7pages).

* cited by examiner

*Primary Examiner* — Allen Porter
*Assistant Examiner* — Skylar Lindsey Christianson
(74) *Attorney, Agent, or Firm* — Buchanan Ingersoll & Rooney PC

(57) ABSTRACT

An implantable device, comprising: an end section, and at least one or a plurality of anchoring elements connected to the end section for anchoring the end section of the implantable device in the tissue of a patient, the anchoring element(s) extending in an extension direction of the anchoring element(s). The anchoring element(s): has an elastically compressible design; can be arranged in a compressed state in which it is folded toward the end section; and is designed to automatically move into an expanded state in which it projects from the end section at an angle of incidence. The anchoring element(s) comprises at least one first lamella and a second lamella connected to the first lamella, and wherein the two lamellae extend along the extension direction of the anchoring element(s) and include a first angle with one another in a plane perpendicular to the extension direction of the anchoring element(s).

16 Claims, 5 Drawing Sheets

PASSIVE FIXATION OF AN IMPLANTABLE ELECTRODE LEAD BY MEANS OF COMPRESSIBLE ANCHORING ELEMENTS

CROSS-REFERENCE TO RELATED APPLICATIONS

This patent application claims the benefit of and priority to co-pending German Patent Application No. DE 10 2018 111 741.8, filed on May 16, 2018 in the German Patent Office, which is hereby incorporated by reference in its entirety.

TECHNICAL FIELD

The present invention relates to an implantable device, comprising an end section of the implantable device, and comprising at least one or more anchoring elements for anchoring the end section of the implantable device in the tissue (such as cardiac tissue) of a patient, wherein the respective anchoring element extends in an extension direction of the respective anchoring element.

BACKGROUND

Usually, either active fixation systems, such as screws, or passive fixation systems, which may include anchoring elements (in particular barbs) made of plastic material, for example, are used to fix implantable electrode leads, for example, in the heart of a patient.

For reliably anchoring the electrode lead in the cardiac tissue, a certain minimum degree of flexural rigidity of the anchoring system is needed. The flexural rigidity depends on the dimensions of the component in the bending direction and the stiffness (modulus of elasticity) of the material used. Less stiff materials require larger dimensions for a predefined flexural rigidity, thereby usually taking up a larger volume. The maximum permissible volume is limited by the inside diameter of the sheath introducer used, which preferably corresponds to the diameter of the electrode lead. As a result, the selection of materials for the fixation system is accordingly limited when the electrode diameter is predefined.

The plastic materials used are usually polyurethane-based or silicone-based polymers. Polyurethanes have the advantage of comparatively high mechanical strength and stiffness, which allows them to be reliably anchored in the cardiac tissue and positioned using a sheath introducer having a small inside diameter. The drawback of polyurethanes is the susceptibility thereof to chemical degradation (in particular oxidative processes).

Silicone-based plastic materials are comparatively inert from a chemical point of view, but compared to polyurethanes have considerably lower material stiffness, so that the geometry of the barbs has to be increased to achieve the same anchoring resistance levels as with polyurethanes. However, larger geometries cannot readily be used for passive fixation systems without increasing the inside diameter of the sheath introducer.

The present invention is directed at overcoming one or more of the above-mentioned problems.

Proceeding from this, it is an object of the present invention to provide an implantable device that allows passive fixation based on chemically inert plastic materials, such as silicone, in such a way that the anchoring element has or the anchoring elements have sufficient flexural rigidity and, in particular, allow the use of conventional sheath introducers.

SUMMARY

At least the above object is achieved by an implantable device having the features of claim 1.

Advantageous embodiments of the present invention are provided in the dependent claims and will be described hereafter.

According to claim 1, an implantable device is disclosed, comprising:
  an end section of the implantable device, which extends in particular along a longitudinal axis; and
  at least one anchoring element or a plurality of anchoring elements, wherein the at least one anchoring element is, or the anchoring elements are, connected to the end section and is, or are, designed to anchor the end section of the implantable device in the tissue of a patient, wherein the at least one anchoring element, or the respective anchoring element, extends in an extension direction.

To the extent that mention is made hereafter of a respective anchoring element, this shall also include the at least one anchoring element in the case where the implantable device comprises at least one anchoring element.

According to the present invention, it is now provided that the respective anchoring element has an elastically compressible design, wherein the respective anchoring element can be arranged in a compressed state in which the respective anchoring element is folded toward the end section, and wherein the respective anchoring element is designed to automatically move toward an expanded state in which the respective anchoring element projects from the end section of the implantable device at an angle of inclination, wherein the respective anchoring element comprises at least one first lamella and a second lamella connected (in particular in one piece) to the first lamella, and wherein the two lamellae extend along the extension direction of the respective anchoring element and include an (in particular obtuse, right or acute) first angle with one another in a plane perpendicular to the extension direction of the respective anchoring element.

In particular, a hook geometry including lamellae is thus used, which meets the requirements with regard to sufficiently high flexural rigidity of the hooks or of the anchoring elements for attachment in the body tissue, while requiring only little material volume. Due to the deformable lamellae, this hook geometry can also be guided bidirectionally through sheath introducers having a small inside diameter. In this way, it becomes possible to use chemically inert, but less stiff plastic materials, such as silicone, for the fixation component, without increasing the volume of the component.

According to one embodiment of the present invention, it is provided that the respective anchoring element is or the lamellae are made of silicone.

According to one further preferred embodiment of the present invention, it is provided that the respective anchoring element is, or the lamellae are, made of polyurethane. Anchoring elements or lamellae that are made of polyurethane have the additional advantage that the geometry of the anchoring elements can be further reduced, which opens up the option of producing electrode leads having a smaller diameter than is possible with silicone, using the described hook geometry including lamellae.

Furthermore, according to a preferred embodiment of the present invention, it is provided that the respective first angle in the compressed state of the respective anchoring element is smaller than in the expanded state of the respective anchoring element.

Furthermore, according to a preferred embodiment of the present invention, it is provided that the respective first angle in the expanded state of the respective anchoring element is 90°.

Furthermore, according to a preferred embodiment of the present invention, it is provided that the respective anchoring element comprises a third lamella and a fourth lamella, wherein the third and fourth lamellae extend along the extension direction of the respective anchoring element and enclose an (in particular obtuse, right or acute) second angle with one another in a plane perpendicular to the extension direction of the respective anchoring element.

According to an embodiment of the present invention, it is provided that the respective second angle is smaller in the compressed state than in the expanded state of the respective anchoring element. According to one embodiment, it is further provided that the respective second angle in the expanded state of the respective anchoring element is 90°.

Furthermore, according to a preferred embodiment of the present invention, it is provided that the first angle and the second angle of the respective anchoring element form vertical angles.

In this regard, it is further preferably provided according to one embodiment of the present invention that the third and fourth lamellae of the respective anchoring element are connected to the first and second lamellae of the respective anchoring element, in particular in one piece, so that the respective anchoring element in the expanded state has a cross-shaped design in a plane extending perpendicularly to the extension direction of the respective anchoring element.

Such a cross-shaped configuration of the respective anchoring element advantageously allows the flexural rigidity of the respective anchoring element to be increased, without the material volume of the respective component or anchoring element being increased. The material selection is thus subject to fewer limitations.

Furthermore, according to one alternative embodiment, it is provided that the respective anchoring element is designed as a hollow profile comprising a peripheral wall, wherein the first and second lamellae of the respective anchoring element each form a portion of the wall of the respective anchoring element.

Furthermore, according to one embodiment it is provided that the wall of the respective hollow profile comprises a third lamella and a fourth lamella, wherein the wall of the respective hollow profile is designed to have a rectangular cross-section with respect to a plane extending perpendicularly to the extension direction of the respective hollow profile.

According to an alternative embodiment of the present invention, it is provided that the wall of the respective hollow profile—apart from the first and second lamellae—comprises a third, a fourth, a fifth and a sixth lamella, wherein the wall of the respective hollow profile is designed to have a hexagonal cross-section with respect to a plane extending perpendicularly to the extension direction of the respective hollow profile.

Furthermore, according to one embodiment of the present invention, it is provided that the end section of the implantable device, on a peripheral outer side, has a recess for receiving the anchoring elements (or the at least one anchoring element) in the compressed state of the anchoring elements (or of the at least one anchoring element). Said recess may be formed by a taper of the end section.

Furthermore, according to one embodiment of the present invention, it is provided that the respective angle of inclination at which the respective anchoring element projects from the end section of the implantable device is in a range of 30° to 85°, and in particular in a range of 50° to 70°.

According to a further embodiment of the present invention, it is provided that the device comprises one to eight anchoring elements, in particular two to eight anchoring elements, and in particular three to four anchoring elements. (See e.g., FIG. 2A).

Furthermore, according to a further embodiment of the present invention, it is provided that the device comprises four anchoring elements, wherein the anchoring elements are arranged equidistantly with respect to one another in the circumferential direction of the end section of the implantable device, that is two adjoining anchoring elements in each case have the same angular separation in the circumferential direction.

According to a further embodiment of the present invention, the implantable device comprises an electrode lead or is designed as an electrode lead, wherein the electrode lead comprises said end section, from which the anchoring elements project or from which the at least one anchoring element projects.

According to a further embodiment, it is provided that the implantable device or the electrode lead comprises an electrode, which is arranged at the end section, wherein the electrode is arranged, in particular, at one end of the electrode lead or of the end section.

Further features, aspects, objects, advantages, and possible applications of the present invention will become apparent from a study of the exemplary embodiments and examples described below, in combination with the Figures, and the appended claims.

DESCRIPTION OF THE DRAWINGS

Other advantages and expedient features of the present invention follow from the following description of sample embodiments, which make reference to the Figures. The Figures are as follows.

DETAILED DESCRIPTION

Figure 1:
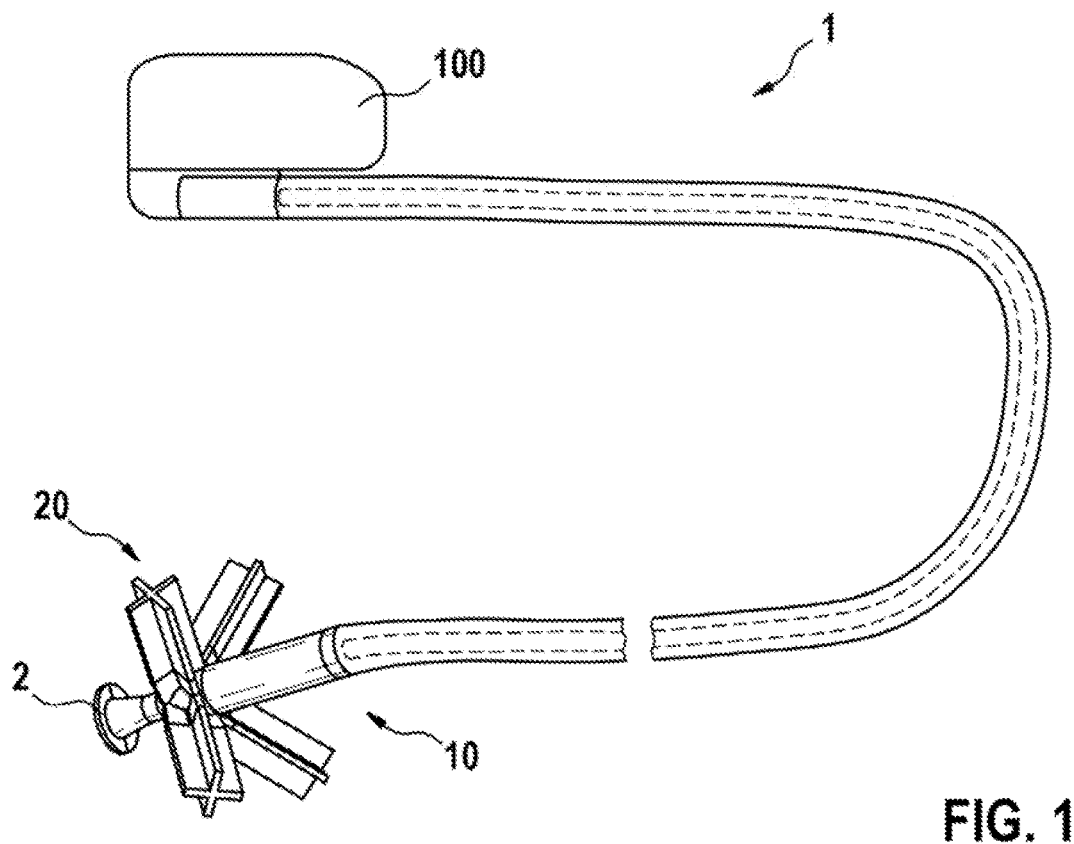
FIG. 1 shows an active implant, having an implantable device connected thereto, including anchoring elements at the end section thereof.

FIG. 1 shows an active implant 100, for example in the form of a cardiac pacemaker, having an implantable device 1, for example in the form of an electrode lead, connected thereto. The device 1 is connected to the implant 100, in particular, via a detachable connection.

Figure 2:
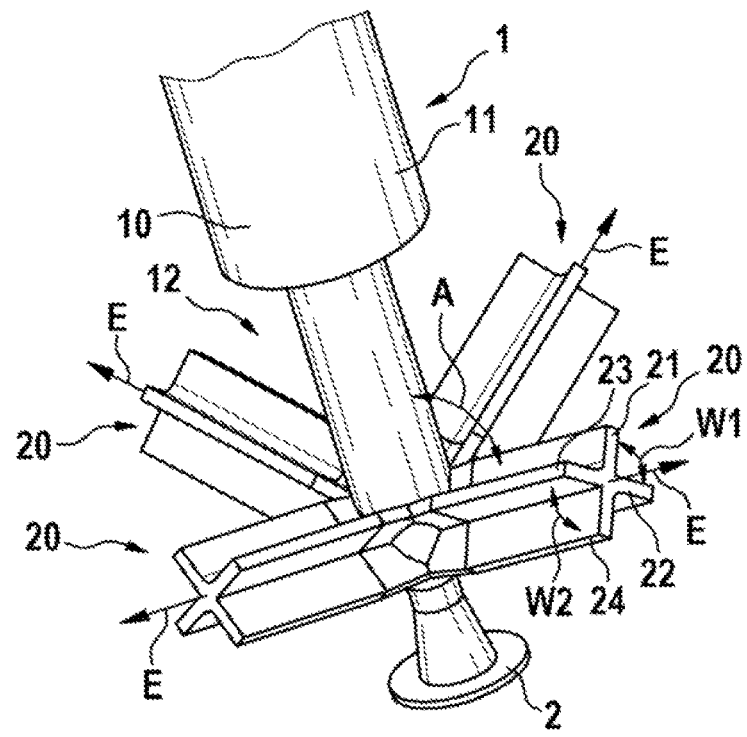
FIG. 2 shows a perspective view of an end section of an implantable device according to the present invention, including anchoring elements.
Figure 2A:
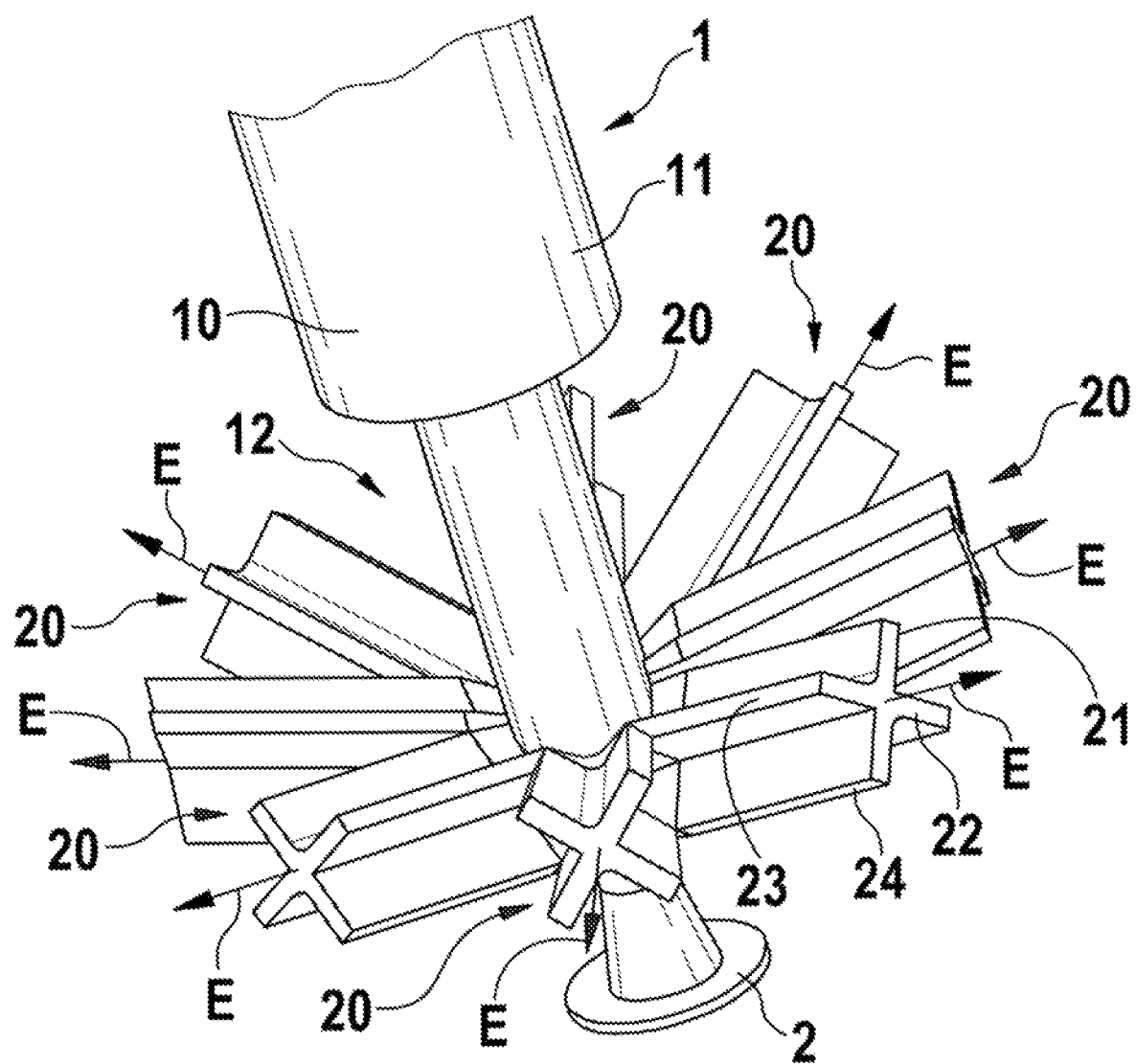
FIG. 2A shows a perspective view of an end section of an implantable device according to an additional embodiment of the present invention, includine anchoring elements.

At the distal end section 10, the implantable device 1 comprises anchoring elements 20. FIG. 2 shows an embodiment of an implantable device 1 according to the present invention, here, for example, in the form of an electrode lead 1 for a cardiac pacemaker, comprising an end section 10 of the implantable device 1, wherein an electrode 2 of the electrode lead 1 is arranged at the distal end of the end section 10 or of the electrode lead 1. The electrode lead 1 further comprises at least one anchoring element 20 connected to the end section 10, wherein the present invention will be described hereafter by way of example based on a plurality of anchoring elements 20 connected to the end section 10, each being used to anchor the end section 10 or the electrode 2 of the implantable device 1 in the tissue of a patient, wherein the respective anchoring element 20 extends in an extension direction E of the respective anchoring element 20.

According to the present invention, it is provided that the respective anchoring element 20 has an elastically compressible design, wherein the respective anchoring element 20 can be arranged in a compressed state in which the respective anchoring element 20 is folded toward the end section 10, and wherein the respective anchoring element 20 is designed to automatically move out of the compressed state thereof into the expanded state in which the respective anchoring element 20 projects from the end section 10 at an angle of inclination A. Furthermore, the respective anchoring element 20 comprises a first lamella 21 (i.e., projection, protusion, flange, etc.) and a second lamella 22 (i.e., projection, protrustion, flange, etc.) connected to the first lamella 21, wherein the two lamellae 21, 22 extend along the extension direction E of the respective anchoring element 20 and enclose a first angle W1 with one another in a plane perpendicular to the extension direction E of the respective anchoring element 20, the angle preferably being 90° in the expanded state of the respective anchoring element. Furthermore, the respective anchoring element 20 preferably comprises a third and fourth lamellae 23, 24, (i.e., projection, protrustion, flange, etc.) wherein the four lamellae 21, 22, 23, 24 are preferably connected to one another (in particular in one piece) so that the respective anchoring element 20 has a cross-shaped cross-section. The third and fourth lamellae 23, 24 of the respective anchoring element 20 enclose a second angle W2, which is likewise preferably 90° in the expanded state of the respective anchoring element. The two angles W1, W2 form vertical angles, wherein the two angles W1, W2 in the compressed state of the respective anchoring element 20, as is apparent from FIGS. 3 and 4, can be more acute than 90°, at least in sections along the respective anchoring element 20.

The cross-shaped configuration of the lamellae 21, 22, 23, 24 ensures sufficient flexural rigidity, wherein in particular a bidirectional configuration of the anchoring system 20 is also present since the electrode lead 1 can essentially be guided in both directions through the sheath introducer (not shown). According to FIG. 2, the device 1 comprises, in particular, four anchoring elements 20, which can be made of silicone, for example, and are symmetrically distributed around the electrode lead 1. The respective angle of inclination of the silicone hooks 20 or anchoring elements 20 in relation to the end section 10 of the electrode lead 1 is preferably in the range of 30° to 85°, and in particular in the range of 50° to 70°.

According to one example, the flexural rigidity of the anchoring elements 20 can be approximately 0.07 $Nmm^2$ in the uncompressed or expanded state.

Figure 4A:
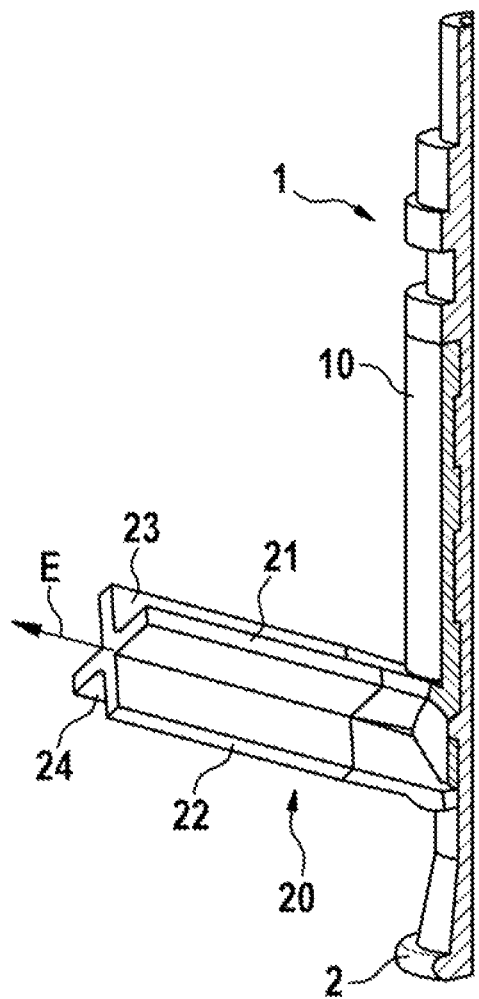
FIGS. 4A-B show a perspective view of an anchoring element in the manner of FIGS. 2 and 3 in the expanded state (A) and in the compressed state (B)
Figure 4B:
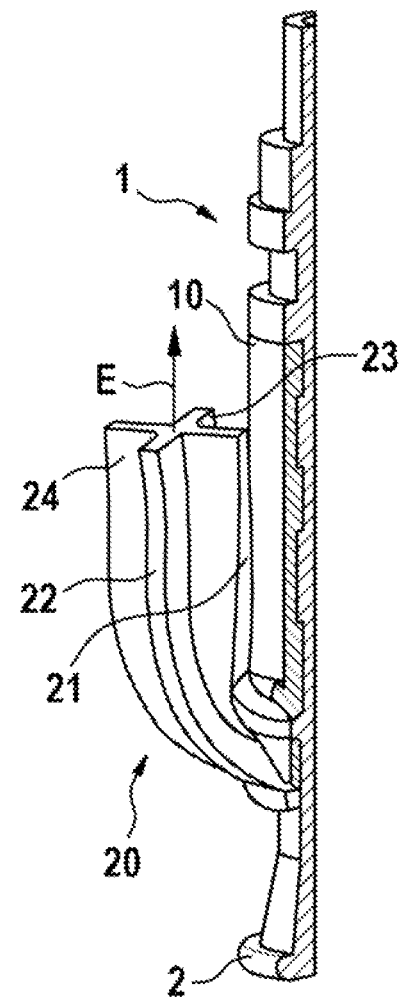

During the insertion of the sheath introducer, a radial force acts on the respective anchoring element 20, pressing this toward the end section 10 or the electrode lead 1 (see FIG. 4B). Since both the respective anchoring element 20 and the lamellae 21, 22, 23, 24 thereof are being bent, the maximum outside diameter of the electrode lead 1 or of the end section 10 corresponds to the inside diameter of the sheath introducer. It is also conceivable for the respective anchoring element 20 to comprise more than four lamellae.

Furthermore, it is preferably provided that the end section 10 of the electrode lead 1, on a peripheral outer side 11 of the end section 10, has a recess 12 for receiving the anchoring elements 20 in the compressed state of the anchoring elements 20.

Figure 5A:
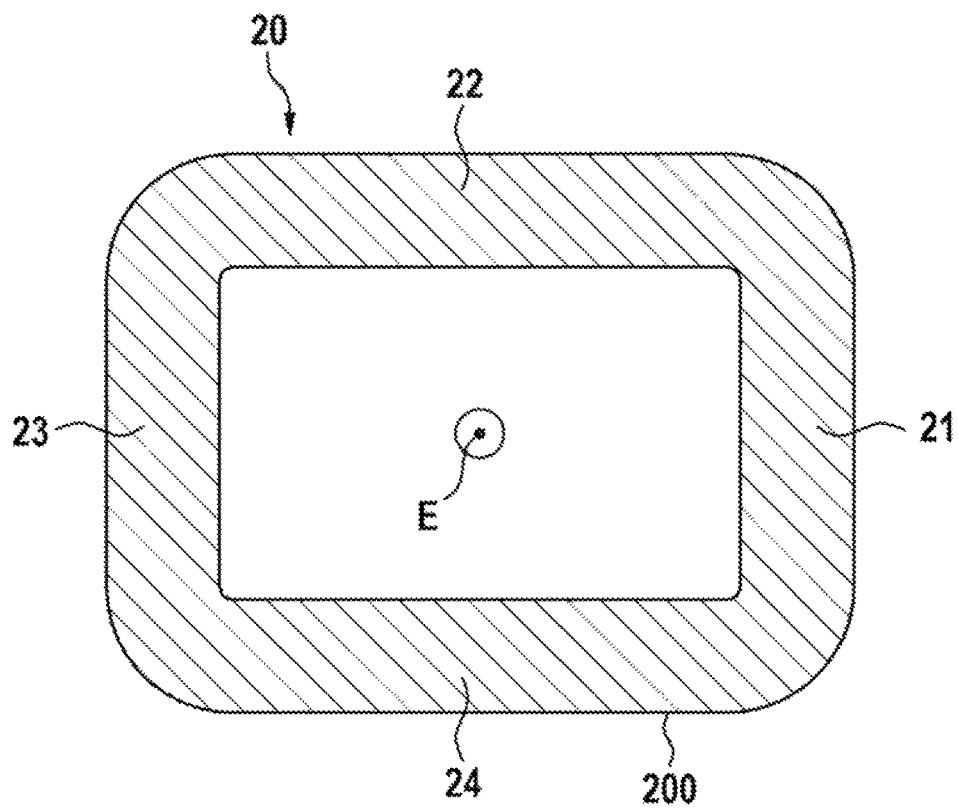
FIGS. 5A-B show a sectional illustration of an anchoring element in the form of a hollow profile (A) having a rectangular cross-section and in the form of a hollow profile (B) having a hexagonal cross-section.
Figure 5B:
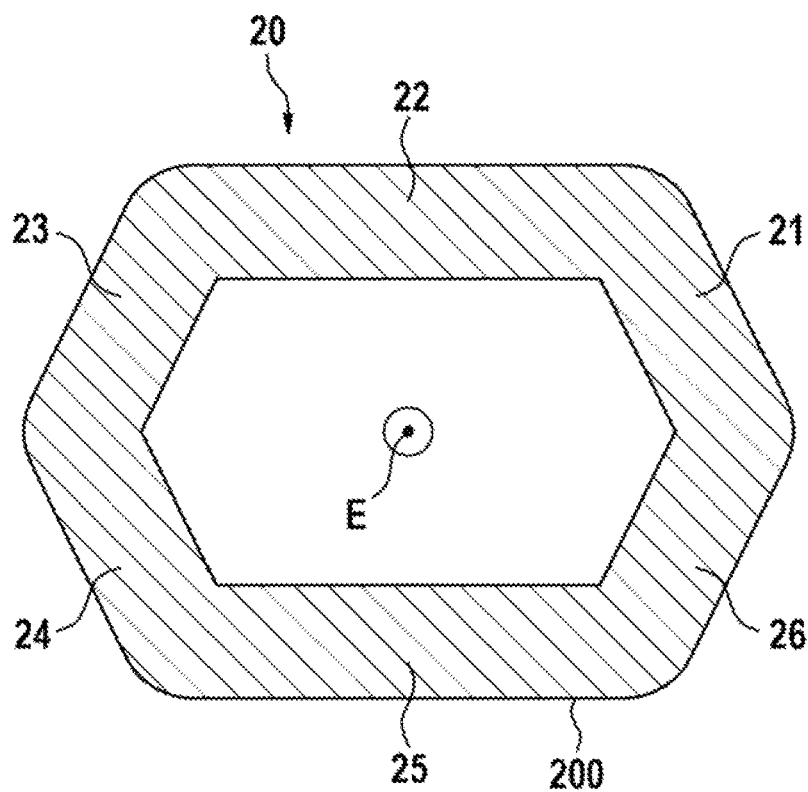

Increased compressibility of the anchoring elements 20 can also be achieved by forming the anchoring elements into hollow bodies or hollow profiles 20, as is indicated in FIG. 5, which shows anchoring elements 20 having a rectangular or square cross-section see FIG. 5A) or anchoring elements 20 having a hexagonal cross-section (see FIG. 5B).

According to FIG. 5A, the respective anchoring element 20 designed as a hollow profile 20 comprises four mutually connected lamellae 21, 22, 23, 24, which form a peripheral wall 200 of the respective hollow profile 20, which has said rectangular or square cross-section in a plane extending perpendicularly to the extension direction E of the respective hollow profile 20 or anchoring element 20.

According to FIG. 5B, the respective anchoring element 20 designed as a hollow profile 20 can also comprise six mutually connected lamellae 21, 22, 23, 24, 25, 26 which form a peripheral wall 200 of the respective hollow profile 20, which has said hexagonal cross-section in a plane extending perpendicularly to the extension direction E of the respective hollow profile 20 or anchoring element 20.

In principle, the anchoring elements 20 can have a length in the range of 2 mm to 4 mm, for example, in all embodiments in the respective extension direction.

Figure 3A:
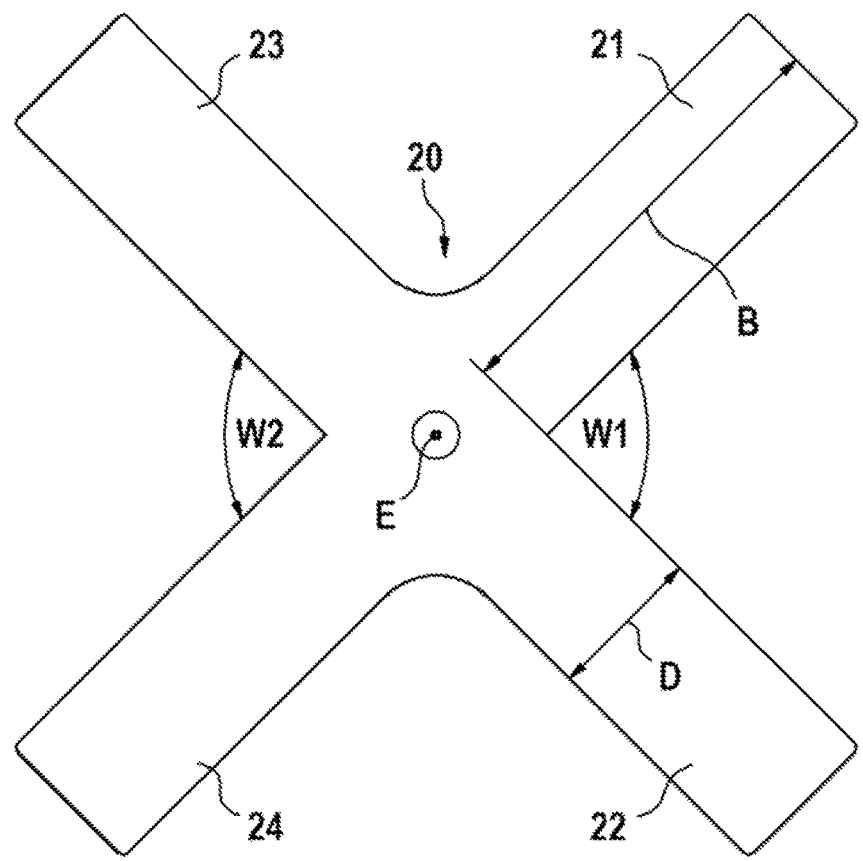
FIGS. 3A-B show a sectional illustration of an anchoring element in the manner of FIG. 2 in the expanded state (A) and in the compressed state (B)
Figure 3B:
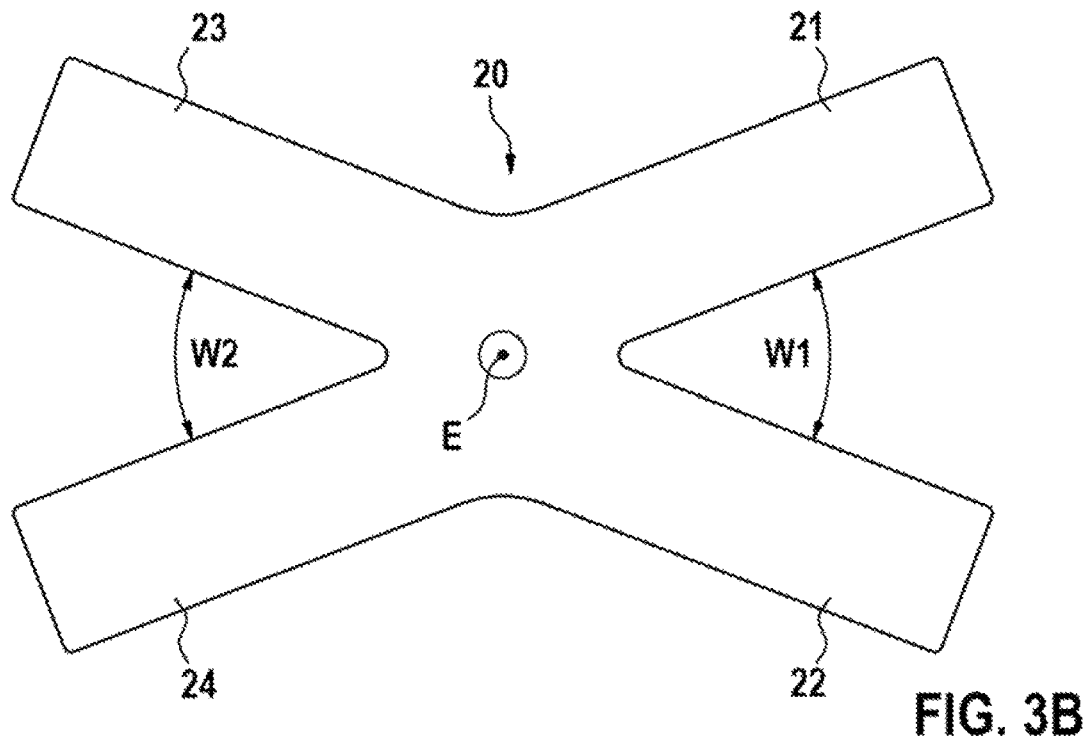

Furthermore, the lamellae 21, 22, 23, 24 according to FIG. 3 or FIG. 5A can each have a width B perpendicular to the respective extension direction E which is in the range of 0.4 mm to 0.6 mm, for example.

Furthermore, the lamellae 21, 22, 23, 24, 25, 26 according to FIG. 5B can each have a width B perpendicular to the respective extension direction E which is in the range of 0.4 mm to 0.6 mm, for example.

Furthermore, the lamellae 21, 22, 23, 24 according to FIG. 3 or FIG. 5A can each have a thickness D which is in the range of 0.1 mm to 0.3 mm.

Furthermore, the lamellae 21, 22, 23, 24, 25, 26 according to FIG. 5B can each have a thickness D which is in the range of 0.1 mm to 0.3 mm.

Furthermore, according to one example of the present invention, it may be provided that the flexural rigidity of the respective anchoring element 20 is in the range of 0.05 $Nmm^2$ to 0.10 $Nmm^2$, for example. Furthermore, the material stiffness of the material used for the anchoring elements 20 can be in the range of 2 $N/mm^2$ to 20 $N/mm^2$.

Furthermore, the lamellae 21, 22, 23, 24, 25, 26 according to FIGS. 2, 3 and 5 can have a cuboid design across the majority of the lengths thereof in the extension direction E, but may also each taper in the connecting region to the electrode lead 1 or the end section 10.

It will be apparent to those skilled in the art that numerous modifications and variations of the described examples and embodiments are possible in light of the above teaching teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An implantable device, comprising:
an end section of the implantable device;
and at least one anchoring element connected to the end section for anchoring the end section of the implantable device in a tissue of a patient, the at least one anchoring element extending in an extension direction of the at least one anchoring element,
wherein the at least one anchoring element has an elastically compressible design, wherein the at least one anchoring element can be arranged in a compressed state in which the at least one anchoring element is folded toward the end section, and wherein the at least one anchoring element is designed to automatically move into an expanded state in which the at least one anchoring element projects from the end section at an angle of inclination, wherein the at least one anchoring element comprises at least one first flange and an immediately adjacent second flange connected to the first flange, and wherein the two flanges each extend along the extension direction of the at least one anchoring element and include a first angle with one another in a plane perpendicular to the extension direction of the at least one anchoring element;
wherein the first angle is smaller in the compressed state than in the expanded state of the at least one anchoring element.

2. The implantable device according to claim I, wherein the at least one anchoring element comprises a third and a fourth flange, wherein the third and fourth flanges each extend along the extension direction of the at least one anchoring element and enclose a second angle with one another in a plane perpendicular to the extension direction of the at least one anchoring element.

3. The implantable device according to claim 2, wherein the second angle is smaller in the compressed state than in the expanded state of the at least one anchoring element.

4. The implantable device according to claim 3, wherein the first angle and the second angle of the at least one anchoring element form vertical angles.

5. The implantable device according to any one of claim 2, wherein the third and fourth flanges of the at least cane anchoring element are connected to the first and second flanges of the at least one anchoring element, so that the at least one anchoring element has a cross design in the expanded state in a plane extending perpendicularly to the extension direction of the at least one anchoring element.

6. The implantable device according to claim 1, wherein the at least one anchoring element is designed as a hollow profile comprising a peripheral wall, wherein the first and second flanges of the at least one anchoring element each form a portion of the peripheral wall of the at least one anchoring element.

7. The implantable device according to claim 6, wherein the peripheral wall of the hollow profile comprises a third and a fourth flange, wherein the peripheral wall of the hollow profile is designed to have a rectangular cross-section.

8. The implantable device according to claim 6, wherein the peripheral wall of the hollow profile comprises third, fourth, fifth and sixth flanges, wherein the peripheral wall of the hollow profile is designed to have a hexagonal cross-section.

9. The implantable device according to claim 1, Wherein the end section, on a peripheral outer side, has a recess for receiving the at least one anchoring element in the compressed state of the at least one anchoring element.

10. The implantable device according to claim 1, wherein the angle of inclination is in a range of 30° to 85°.

11. The implantable device according to claim 1, wherein the at least one anchoring element. comprises one to eight anchoring elements.

12. The implantable device according to claim 1, wherein the at least one anchoring element comprises two to eight anchoring elements.

13. The implantable device according to claim 1, wherein the at least anchoring element comprises three to four anchoring elements.

14. The implantable device according to claim 1, wherein the at least one anchoring element comprises four anchoring elements.

15. The implantable device according to claim 1, wherein the implantable device is an electrode lead.

16. The implantable device according to claim 1, wherein the implantable device comprises an electrode, which is arranged on the end section.

* * * * *